(12) United States Patent
Widman et al.

(10) Patent No.: US 8,644,901 B2
(45) Date of Patent: Feb. 4, 2014

(54) SYSTEM AND METHOD OF RESOLVING OUTLIERS IN NIRS CEREBRAL OXIMETRY

(75) Inventors: Ronald A. Widman, Macomb, MI (US); Arik Anderson, Birmingham, MI (US); Oleg Gonopolskiy, West Bloomfield, MI (US)

(73) Assignee: Covidien LP, Mansfield, MA (US)

( * ) Notice: Subject to any disclaimer, the term of this patent is extended or adjusted under 35 U.S.C. 154(b) by 338 days.

(21) Appl. No.: 13/033,568

(22) Filed: Feb. 23, 2011

(65) Prior Publication Data

US 2011/0208024 A1   Aug. 25, 2011

Related U.S. Application Data

(60) Provisional application No. 61/307,175, filed on Feb. 23, 2010, provisional application No. 61/317,795, filed on Mar. 26, 2010.

(51) Int. Cl.
*A61B 5/1455* (2006.01)

(52) U.S. Cl.
USPC ........................................... 600/323

(58) Field of Classification Search
USPC .................. 600/310, 322, 323, 336
See application file for complete search history.

(56) References Cited

U.S. PATENT DOCUMENTS

| | | | | |
|---|---|---|---|---|
| 4,714,341 A | * | 12/1987 | Hamaguri et al. | 600/310 |
| 5,720,284 A | * | 2/1998 | Aoyagi et al. | 600/322 |
| 6,157,850 A | * | 12/2000 | Diab et al. | 600/323 |

* cited by examiner

*Primary Examiner* — Eric Winakur

(57) ABSTRACT

A system and method for non-invasively estimating the tissue blood oxygen saturation level of a human subject, including so-called "outliers", whose physiological make-up causes previously-known techniques to generate invalid tissue blood oxygen saturation estimations. The system includes a computing device and a sensor. The sensor includes a light source configured to emit light of at least four different wavelengths, one at a time. The sensor also includes two light detectors, each positioned a different distances from the light source. Optical density measurements are taken by the light detectors and provided to the computing device. A first tissue blood oxygen saturation value is computed using the optical density measurements associated with three of the four wavelengths, and a second tissue blood oxygen saturation value is computed using the optical density measurements associated with four of the wavelengths. The first and second tissue blood oxygen saturation values are compared, and the human subject is identified as an "outlier" based upon that comparison.

10 Claims, 6 Drawing Sheets

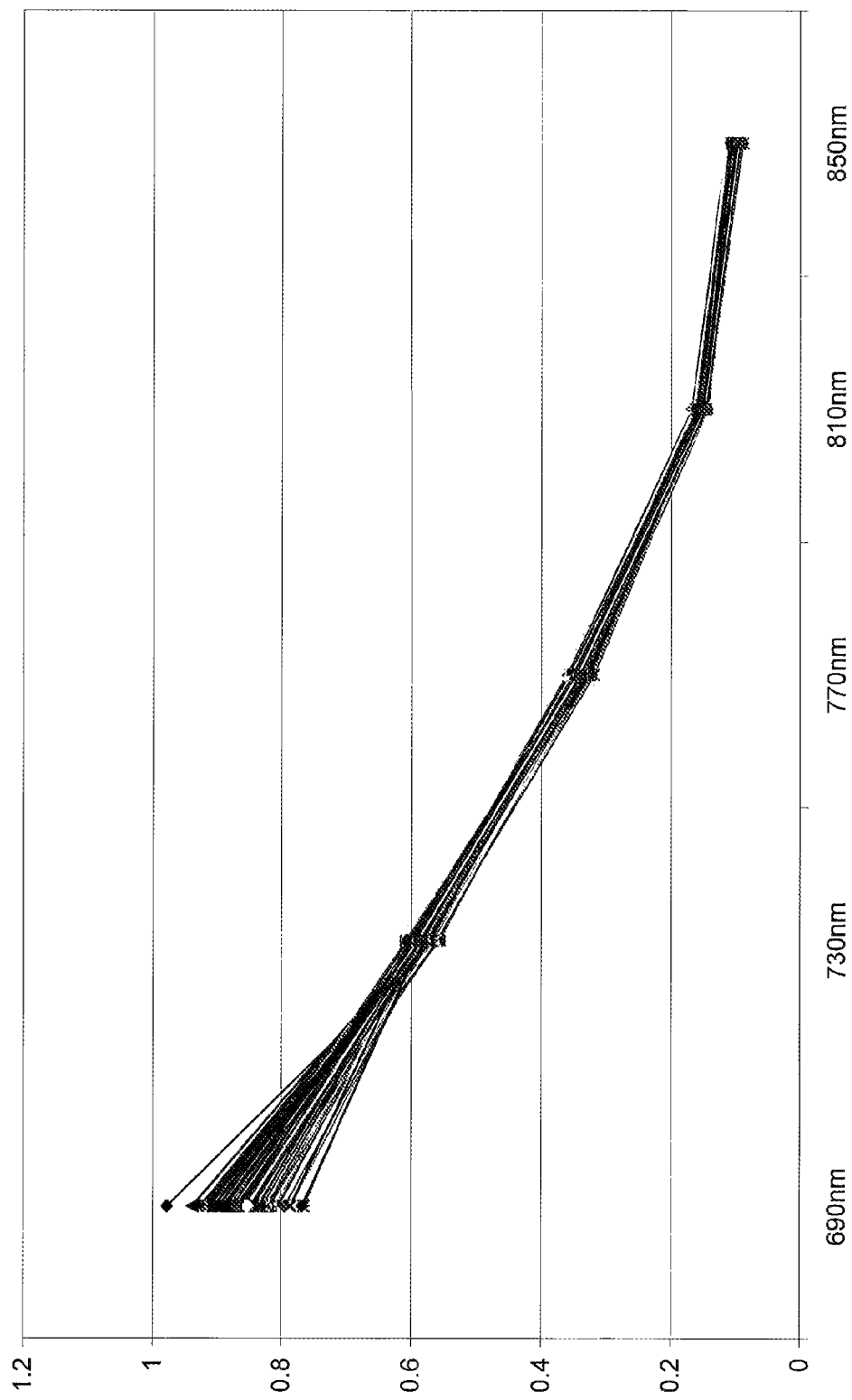
Fig. 4 The space contrasted optical densities Deep-Shallow at different wavelengths for the outlier

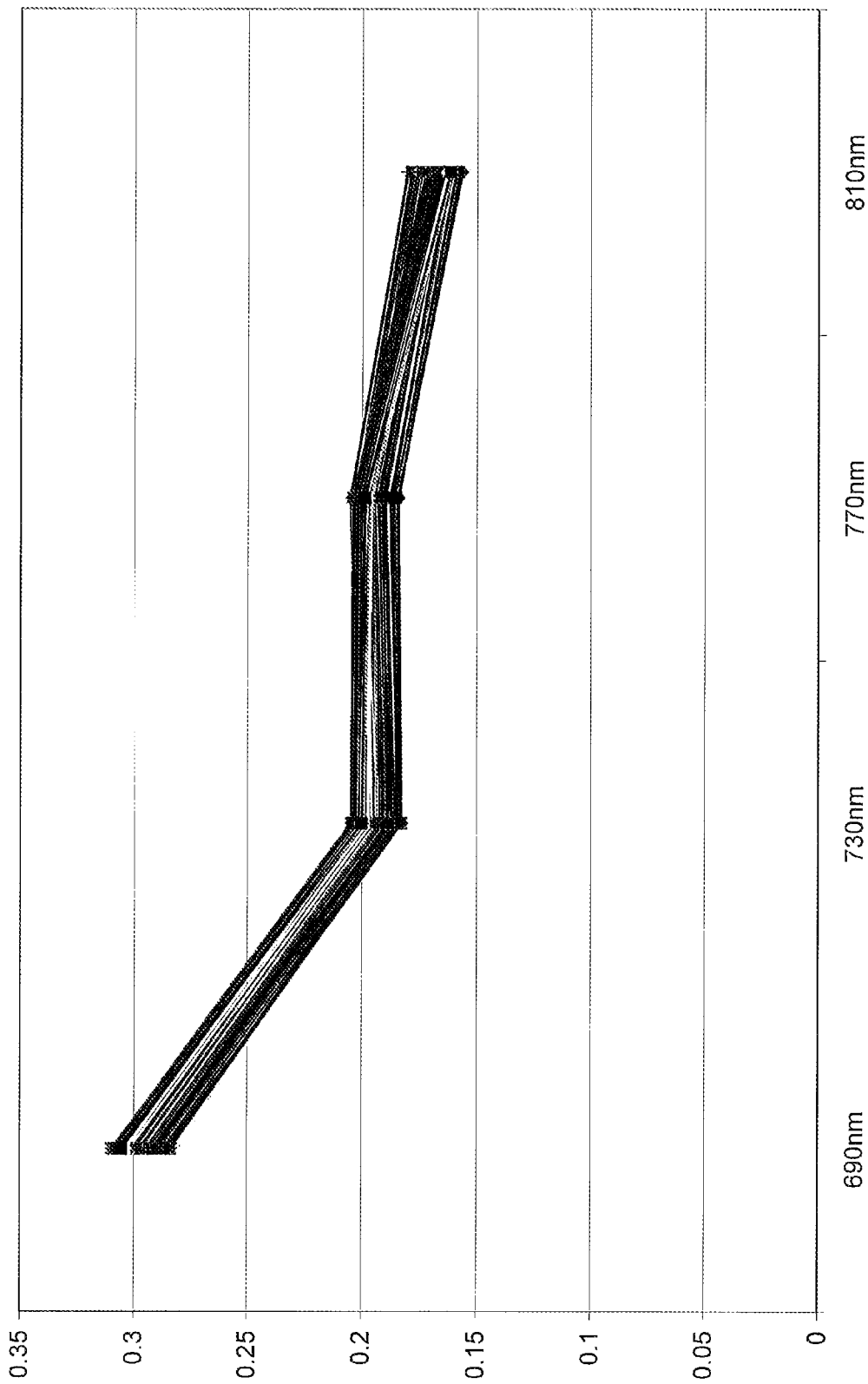

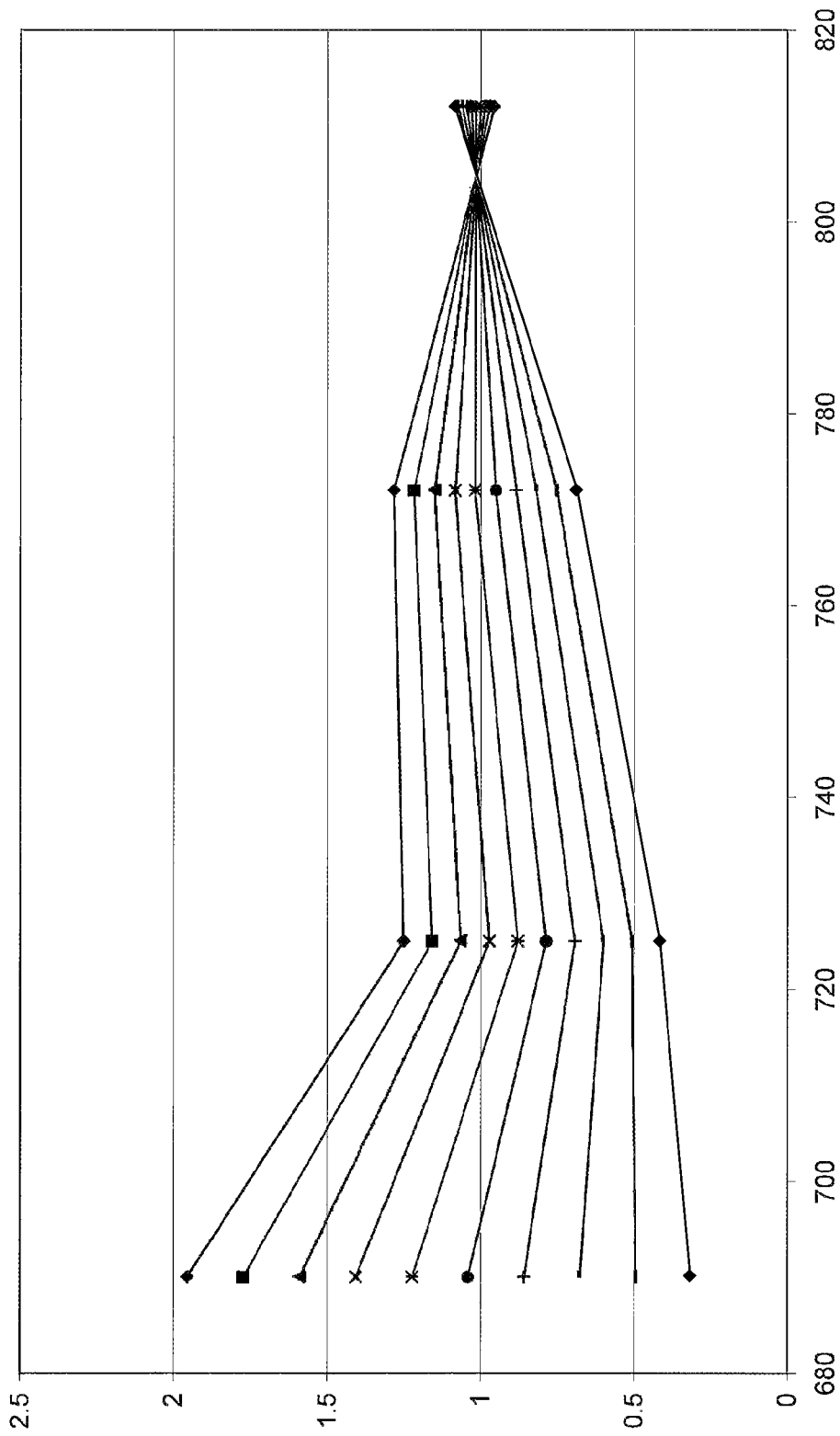
Fig. 6 Optical density of the hemoglobin solution at different O2 saturation at wavelengths 690nm, 730nm, 770nm, 810nm

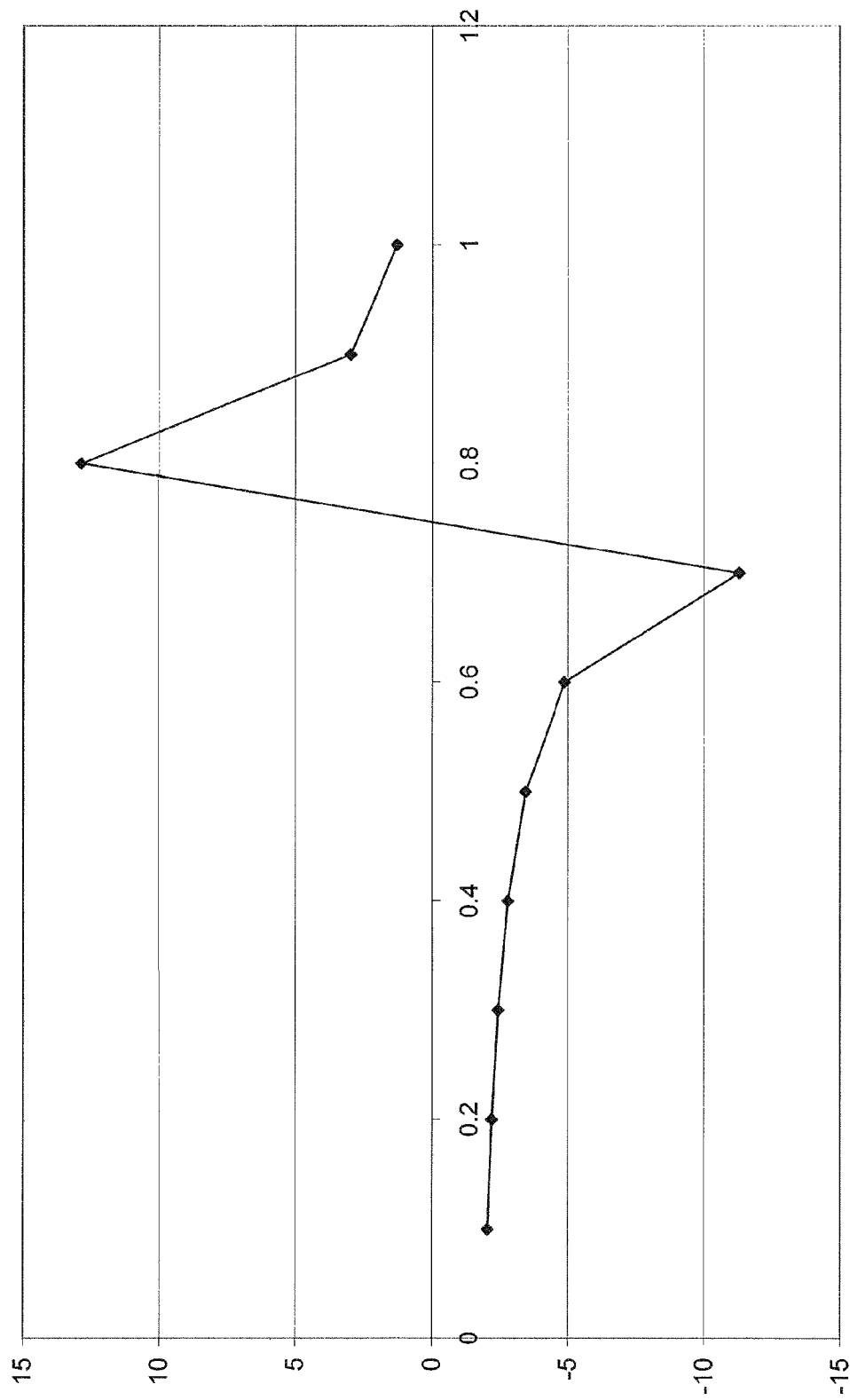
Fig. 7 Hemoglobin wide gap 2nd derivative ratio versus rSO2

SYSTEM AND METHOD OF RESOLVING OUTLIERS IN NIRS CEREBRAL OXIMETRY

CROSS-REFERENCE TO RELATED APPLICATIONS

This Application claims the benefit of U.S. Provisional application No. 61/307,175 filed on Feb. 23, 2010 and U.S. Provisional Application No. 61/317,795 filed on Mar. 26, 2010, the entirety of which are hereby incorporated by reference.

BACKGROUND

It is desirable to be able to non-invasively estimate the tissue blood oxygen saturation (rSO2) level in a human subject's brain. It is known that the cerebral tissue blood oxygen saturation level can be non-invasively estimated using near infrared spectrophotography (NIRS). A system and method for performing spatially resolved NIRS to measure cerebral tissue blood oxygen saturation (rSO2) was disclosed in U.S. Pat. No. 5,139,025, U.S. Pat. No. 5,482,034, and U.S. Pat. No. 5,217,013. In general, those patents describe calculating cerebral tissue blood oxygen saturation (rSO2) as a weighted sum of the venous [$HbO_2$] and arterial [Hb] blood oxygen saturations according to the following equation: $rSO_2 = [HbO_2]/([HbO_2]+[Hb])$.

In the known system and method, a sensor having a light source and two light detectors, each spaced a different distance from the light source, is affixed to the forehead of a human subject. The light detector positioned closer to the source is referred to as the "near" or "shallow" detector and the light detector positioned further from the source is referred to as the "far" or "deep" detector. Light of three different wavelengths is selectively introduced into the subject's head, one wavelength at a time. The optical density (OD) of the reflected light of each wavelength is detected by both the "shallow" and the "deep" detectors. That data is used to calculate a so-called space contrasted ratio of the wavelength contrast difference according to the following equation:

$$OD'_{Deep-Shall}(\lambda 1)/OD'_{Deep-Shall}(\lambda 2)$$

where $OD'(\lambda) = OD(\lambda) - OD(\lambda+\Delta)$ is the wavelength contrasted optical density that can be described as a wavelength contrast difference of the optical density $OD(\lambda)$. In addition, $OD_{Deep-Shall}(\lambda) = OD_{Deep}(\lambda) - OD_{Shallow}(\lambda)$ is the spatial contrasted optical density that is the difference of the optical density measured by the far detector $OD_{Deep}(\lambda)$ and the near detector $OD_{Shallow}(\lambda)$ at wavelength $\lambda$. This space contrasted ratio of the wavelength contrast difference can be compared to empirical data to estimate the cerebral tissue blood saturation ($rSO_2$) level of the human subject.

This approach is non-invasive and provides an accurate determination of the $rSO_2$ level of most human subjects. However, it is has been observed that this approach results in invalid $rSO_2$ estimations in approximately 1-2% of human subjects who have normal $rSO_2$ levels, customarily referred to as "outliers." For outliers, the above-described approach for estimating $rSO_2$ results in a reported estimation that is significantly lower than the person's actual $rSO_2$ level. There is evidence that melanin or a melanin-like (or melanin-based) polymer chromophore localized in the connective tissue that covers the brain may be responsible for outliers. While such polymers that are by products of tyrosine degradation are present in normal individuals, in individuals with alkaptonuria they accumulate excessively in the connective tissues. Depending on the amount of the melanin-like polymers in the brain membranes, the $rSO_2$ baseline measured using three wavelengths can be as low as 15%-20%, significantly less than the average normal $rSO_2$ value of 70%. The presence of other chromophores may also be responsible for outliers.

Additionally, there is evidence that patients with liver disease can have a substantial amount of conjugated bilirubin present in their blood and tissues. While unconjugated bilirubin does not interfere with NIRS measurements, conjugated bilirubin preferentially absorbs in the 700 nm-770 nm range and can adversely affect accuracy of the above-described approach for estimating $rSO_2$.

Accordingly, there is a need for an improved system and method for estimating cerebral tissue oxygen saturation ($rSO_2$) levels in human subjects that is capable of identifying outliers and accurately estimating the cerebral tissue oxygen saturation levels for such outliers.

BRIEF SUMMARY OF THE INVENTION

A system for assessing tissue blood oxygen saturation levels is disclosed. The system has a computing device and a sensor in communication with the computing device. The sensor is configured to be attached to a human subject and has a light source capable of selectively emitting at least four different wavelengths of light, one wavelength at a time. The sensor also has a first light detector positioned a first distance from said light source and a second light detector positioned a second distance from said light source, the second distance being greater than the first distance. The computing device has a memory for storing an algorithm and a processor for executing instructions associated with said algorithm.

The algorithm has the following steps. The light source emits light of at least four different wavelengths, one wavelength at a time, into a human subject. The computing device receives optical density measurements from said first and second light detectors for each of the four wavelengths. The computing device estimates a first tissue blood oxygen saturation value based on the optical density measurements associated with three of said four wavelengths. The computing device estimates a second tissue blood oxygen saturation value based the optical density measurements associated with four of said wavelengths. Finally, the computing device determines if said first tissue blood oxygen saturation value is a valid estimate of an actual tissue blood oxygen saturation level in said human subject based upon a comparison of said first tissue blood oxygen saturation value and said second blood oxygen saturation value.

BRIEF DESCRIPTION OF THE DRAWINGS

FIG. 4 is a graph illustrating empirical data showing the space contrasted optical densities at different wavelengths for an "outlier."

FIG. 5 is a graph illustrating empirical data showing the space contrasted optical densities at different wavelengths for a normal subject.

FIG. 6 is a graph illustrating empirical optical densities of hemoglobin solution at different oxygen saturation levels at different wavelengths.

FIG. 7 is a graph illustrating second order optical density ratios for hemoglobin relative to rSO$_2$.

DETAILED DESCRIPTION

Figures 1, 2:
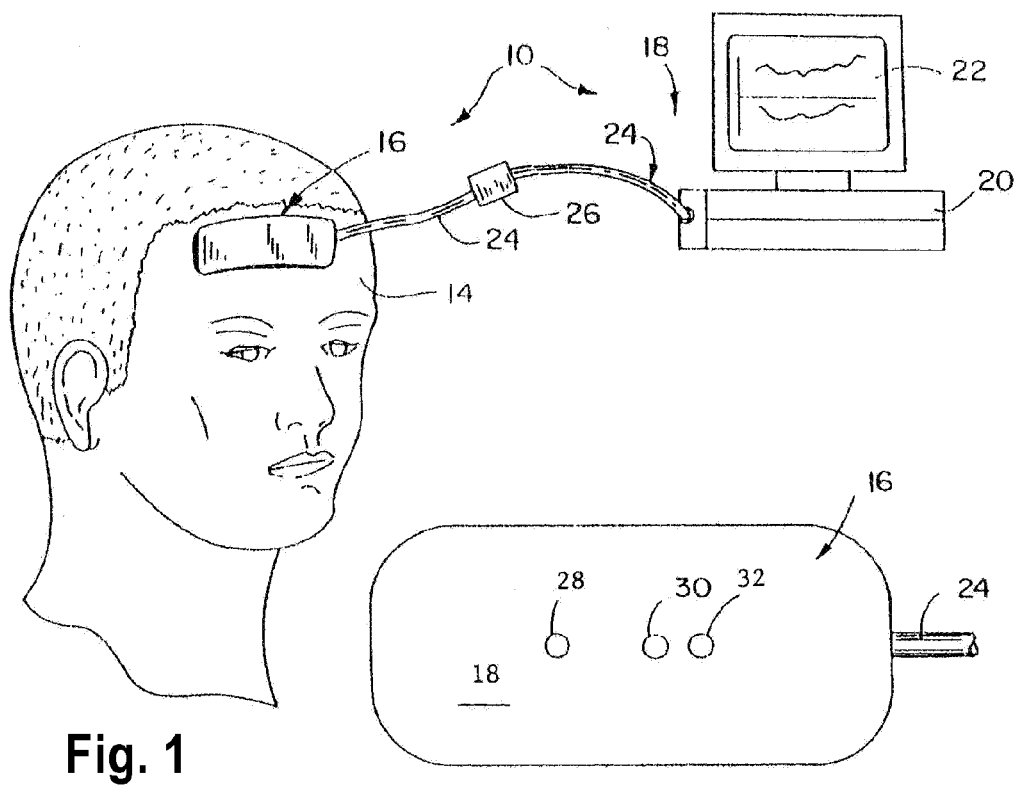
FIG. 1 is an illustrative example of a system according to an embodiment, as used in one exemplary environment to perform spectrophotometric cerebral oximetry.
FIG. 2 illustrates in more detail an exemplary sensor that can be used in the system of FIG. 1.

FIG. 1 illustrates an exemplary environment for implementation of a system 10 to perform spectrophotometric cerebral oximetry. The system 10 has a spectrophotometric apparatus 18 connected to a sensor 16 through an electrical cable 24. The electrical cable 24 may include a signal amplifier 26. The spectrophotometric apparatus 18 is a computer or other processor-based computing device 20 and a monitor or other visual display device 22. The computing device 20 includes customary memory devices that store data and algorithm instructions and a processor that executes algorithm instructions.

FIG. 1 illustrates one exemplary environment for system 10, wherein the sensor 16 is affixed to the forehead 14 of a human subject. The sensor 16 is configured to emit light into the subject's body, receive/detect the light reflected from the subject's body and convert the received light to electrical signals representative of the optical density ("OD") of the received light. The spectrophotometric apparatus 18 is configured to receive the electrical signals from the sensor through the cable 24 and to process those signals using programmed algorithms to generate computed data related to the physiological condition of the human subject. The spectrophotometric apparatus 18 is further configured to display information on the monitor or other visual display 22.

FIG. 2 provides a more detailed illustration of an exemplary sensor 16, The sensor 16 includes a flexible and compliant pad 18 configured to be affixed to a human subject. The sensor 16 includes a light source 28 capable of selectively emitting light having, at any given time, one of at least four different wavelengths. The light source 28 may be implemented in a variety of ways known in the art, such as by using wavelength-specific light emitting diodes. The sensor 16 also includes at least two light detectors 30, 32. The light detectors 30, 32 may also be implemented in a variety of ways known in the art, such as using photodiodes or other photodetectors. The light detectors 30, 32 are physically positioned on the sensor 16 particular distances from the source 28 such that "far" or "deep" detector 32 is positioned further away from the light source 28 than "near" or "shallow" detector 30. The relative distances between the source 28 and the detectors 30 and 32 may differ, but it has been determined that, for cerebral oxygen determination, the "near" or "shallow" detector 30 may be positioned at about 3 centimeters away from the source 28 and the "far" or "deep" detector 32 may be positioned at least about 1 centimeter distant from the "near" or "shallow" detector 30 (about 4 centimeters from the light source 28). Additional details relating to embodiments of sensors 16 are disclosed in U.S. Pat. No. 5,139,025, U.S. Pat. No. 5,482,034, and U.S. Pat. No. 5,217,013, all of which are hereby incorporated by reference.

When in use, the system 10 functions as described below, with reference to the illustrative flowchart in FIG. 3. First (step 100 in FIG. 3), optical density (OD) values are measured at the "near" detector 30 and the "far" detector 32 for each of the at least four wavelengths. Accordingly, in response to control signals generated and sent by spectrophotometric apparatus 18, light source 28 on sensor 16 selectively emits light of at least four different wavelengths into the body of the subject, one wavelength at a time. For example, in one embodiment, the four different wavelengths are $\lambda 1-\Delta=690$ nm, $\lambda 1=730$ nm, $\lambda 2=770$ nm and $\lambda 2+\Delta=810$ nm. The wavelengths are chosen to have a constant gap $\Delta$ between them, which, in this exemplary embodiment equals 40 nm. Other possible wavelengths may be selected. For each wavelength introduced into the subject's body, the optical density ("OD") of the reflected light is detected and measured by both the "near" or "shallow" detector 30 and the "far" or "deep" detector 32 of sensor 16. The detected optical densities are conveyed as electrical signals to the spectrophotometric apparatus 18, where they are processed by an algorithm (stored in memory) executed by the processor to generate useful physiological information related to cerebral tissue blood oxygen saturation (rSO$_2$).

Next (step 110 of FIG. 3), the measured OD values are used to calculate a space contrasted ratio of the wavelength contrast difference of the optical density, applying equations used in known methods for calculating estimated blood oxygen saturation (rSO$_2$) values. Specifically, a space contrasted ratio of the wavelength contrast difference is calculated according to the following equation:

$$OD'_{Deep-Shall}(\lambda 1)/OD'_{Deep-Shall}(\lambda 2) \quad (1)$$

where $OD'(\lambda)=OD(\lambda)-OD(\lambda+\Delta)$ is the wavelength contrasted optical density that can be described as a wavelength contrast difference of the optical density $OD(\lambda)$. In addition, $OD_{Deep-Shall}(\lambda)=OD_{Deep}(\lambda)-OD_{Shallow}(\lambda)$ is the spatial contrasted optical density that is the difference of the optical density measured by the far detector $OD_{Deep}(\lambda)$ and the near detector $OD_{Shallow}(\lambda)$ at wavelength $\lambda$. In the particular example given herein, $OD'_{Deep-Shall}(\lambda 1)=[OD_{Deep}(730)-OD_{Shall}(730)]-[OD_{Deep}(770)-OD_{Shall}(770)]$ and $OD'_{Deep-Shall}(\lambda 2)=[OD_{Deep}(770)-OD_{Shall}(770)]-[OD_{Deep}(810)-OD_{Shall}(810)]$. The space contrasted ratio of $OD'_{Deep-Shall}(\lambda 1)/OD'_{Deep-Shall}(\lambda 2)$ can be used according to methods known in the art to estimate the blood oxygen saturation (rSO$_2$) value, by, for example, comparing the space contrasted ratio to empirical data correlating the space contrasted ratio to cerebral tissue blood oxygen saturation (rSO$_2$) levels.

Next (step 120 of FIG. 3), the measured OD values (i.e., four different wavelengths at both the far and the near light sensors) are used to calculate a second order contrasted optical density ratio, which is also used to estimate a blood oxygen saturation (rSO$_2$) value. This second rSO$_2$ value will be compared to the first rSO$_2$ value estimated from the space contrasted ratio of the wavelength contrast difference (from Equation (1)), as described hereinafter, to determine if the human subject is an "outlier." FIG. 4 and FIG. 5 are graphs that depict exemplary empirical space contrasted optical densities for an outlier (FIG. 4) and a non-outlier (FIG. 5) measured using the four wavelengths 690 nm, 730 nm, 770 nm, 810 nm in the normal condition. It is evident from these graphs that the outlier's profiles do not have the S shape in the 690 nm-810 nm wavelength band as the non-outlier does. This "S" shape of the optical density originates from the absorption profile of the deoxygenated hemoglobin that is shown on FIG. 6. The divergence of the optical density from the specific deoxygenated hemoglobin "S" shape can be identified using second order contrasted optical density, which is calculated according to the following equation:

$$OD''_{Deep-Shall}(\lambda)=OD_{Deep-Shall}(\lambda+\Delta)-2*OD_{Deep-Shall}(\lambda)+OD_{Deep-Shall}(\lambda-\Delta) \quad (2)$$

The second order contrasted optical density reflects the curvature of the optical density. In the particular example given herein, $OD''_{Deep-Shall}(730)=OD_{Deep-Shall}(770)-2*OD_{Deep-Shall}(730)+OD_{Deep-Shall}(690)$. FIG. 7 shows that for non-outliers the $OD''_{Deep-Shall}(730 \text{ nm})$ is positive and $OD''_{Deep-Shall}(770 \text{ nm})$ is negative and for the outliers the $OD''_{Deep-Shall}(730 \text{ nm})$ and $OD''_{Deep-Shall}(770 \text{ nm})$ are very close to zero. To facilitate comparison of the second order differences, they are scaled using the second order difference at a different wavelength (Equation 3) or the first order difference at the same wavelength or a different wavelength (Equation 4)

$$OD''_{Deep-Shall}(\lambda)/OD''_{Deep-Shall}(\lambda+\Delta) \quad (3)$$

$$OD''_{Deep-Shall}(\lambda)/OD'_{Deep-Shall}(\lambda+\Delta) \quad (4)$$

Alternatively, the second order difference can be scaled using an empirical constant B, such as according to the following Equation 5:

$$OD''_{Deep-Shall}(\lambda)/[OD_{Deep-Shall}(\lambda+\Delta)+B] \quad (5)$$

Regardless of the method used (i.e., Equations (3), (4) or (5)), the resulting ratio is the second order contrasted optical density ratio. The second order contrasted optical density ratio is compared to empirical or modeled data of the second order contrasted optical density ratio to blood oxygen saturation ($rSO_2$) to determine an estimated $rSO_2$ of the human subject (step 125 of FIG. 3).

Figure 3:
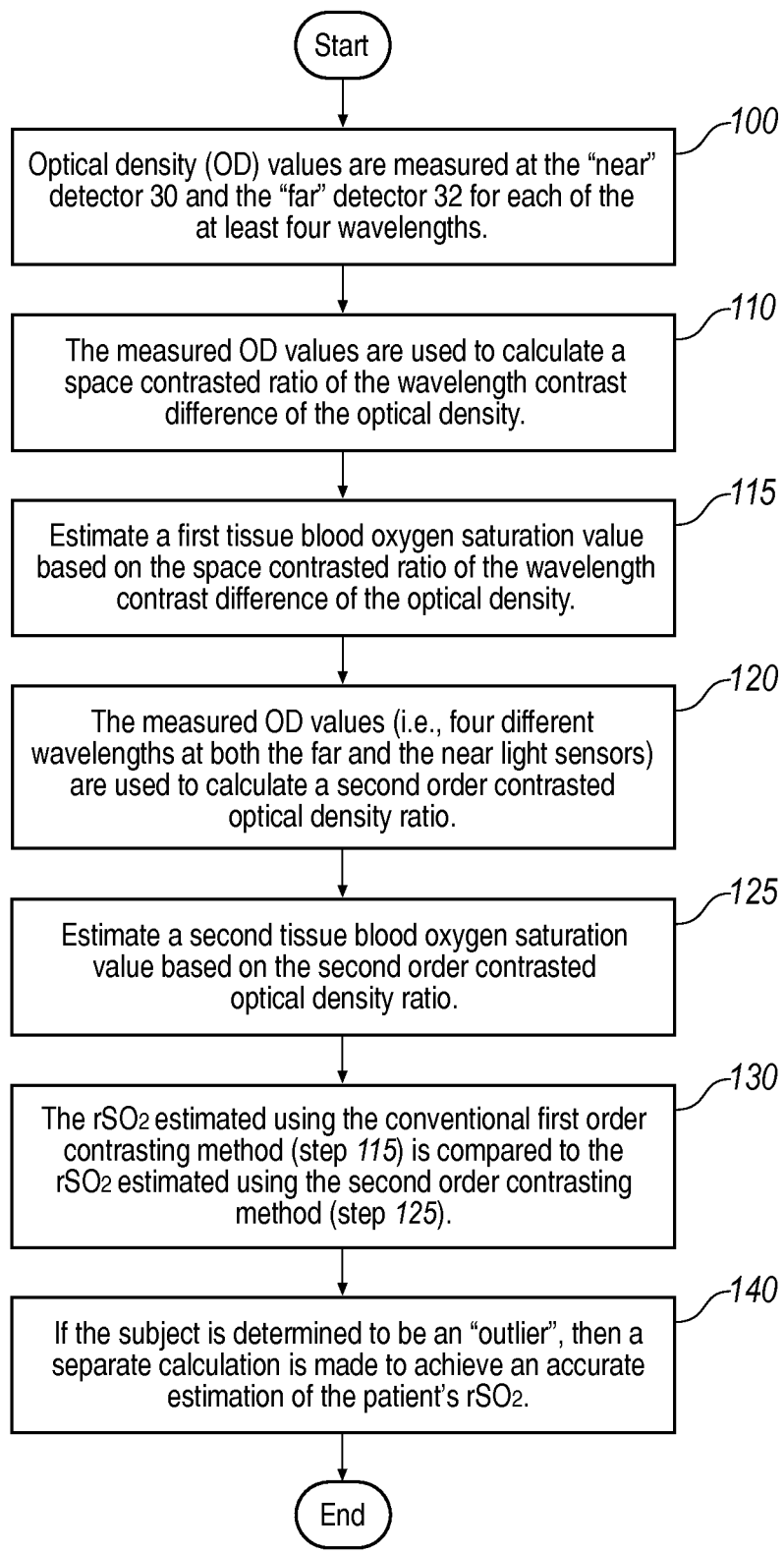
FIG. 3 is a flowchart illustrating exemplary steps in an algorithm used to implement an embodiment.

Next (step 130 of FIG. 3), the $rSO_2$ estimated using the conventional first order contrasting method (step 115 of FIG. 3) is compared to the $rSO_2$ estimated using the second order contrasting method (step 125 of FIG. 3). If the two $rSO_2$ values are about the same, i.e., within about 10%, then it is determined that the human subject is not an outlier, and the estimated $rSO_2$ value using the first order contrasting method (step 115 of FIG. 3) accurately reflects the actual $rSO_2$ of the human subject. If, on the other hand, the two $rSO_2$ values are significantly different, e.g., more than about 10% different, then it is determined that the human subject is an "outlier," and the $rSO_2$ value estimated using the conventional first order contrasting method (step 115 of FIG. 3) is invalid. A visual indication that the subject is an "outlier" may be displayed on the monitor or display device 22.

Next (at step 140 of FIG. 3), if the subject is determined to be an "outlier", then a separate calculation can be made to achieve an accurate estimation of the patient's $rSO_2$ using one of two methods. The first method involves the use of one additional wavelength above 837 nm. Because for melanin and other interfering substances the light absorption falls to zero above 837 nm, it is possible to accurately estimate $rSO_2$ and to correct for non-linear background by measuring the tissue absorption at a wavelength greater than 837 nm.

The second method involves an explicit use of the background spectra characteristic. The melanin and melanin-like compounds introduce the nonlinear background in the optical absorption spectra due to the exponential tail in the near-infrared band 700 nm-837 nm: OD melanin $(\lambda)=C*\exp(-\lambda/b)$ where $b\approx 200$ nm representing a variety of melanin-like polymers or other substances such as bilirubin with a long tail in the near infrared band, C is a constant that is proportional to the concentration and the path of light.

To remove the nonlinear background we can modify the contrasted value as:

$$OD''_{Deep-Shall}(\lambda)=[OD_{Deep-Shall}(\lambda+\Delta)-OD_{Deep-Shall}(\lambda)]-A*[OD_{Deep-Shall}(\lambda)-OD_{Deep-Shall}(\lambda-\Delta)]$$

Where A is the empirical constant specific for the melanin and melanin like compounds. The constant A reflects the relative difference between the background absorption in the $(\lambda+\Delta; \lambda)$ and $(\lambda, \lambda-\Delta)$ bands. It can be estimated as $A=[\exp(-\Delta/b)-1]/[\exp(+\Delta/b)-1]$. It may also include compensation for the wavelength dependence of the path of light if the coefficient A modified as follows:

$$A=\{DPF(\lambda+\Delta/2)/DPF(\lambda-\Delta/2)\}*\{[\exp(-\Delta/b)-1]/[\exp(+\Delta/b)-1]\}$$

Where DPF $(\lambda+\Delta/2)$ is the differential path length factor (DPF), defined as the mean distance traveled by the photons divided by the distance between the points where light entered and left the head for the wavelength within interval $[\lambda+\Delta, \lambda]$. The DPF $(\lambda-\Delta/2)$ is the differential path length factor (DPF) for the wavelength within interval $[\lambda, \lambda-\Delta]$. The typical value of the DPF was found to linearly depend on the wavelength and to be within 7-4 for the wavelengths 690 nm-850 nm.

FIG. 7 shows the plot of the scaled second order difference optical density (1) of the hemoglobin solution at different level of the oxygen saturation. From FIG. 7 we can see that the value of the scaled second derivative is within −2 and −5 when saturation is varied from 0 to 60%. If the optical data are corrupted by presence of an additional chromophore other than hemoglobin, the calculated value of the scaled second derivative will be outside the interval [−2; −5] when the standard calculation using the equation (1) will give $rSO_2$ value within 0-60%.

For the data on FIG. 7 $OD''_{Deep-Shall}$ (730 nm)/$OD''_{Deep-Shall}$ (770 nm)=0.3 indicating the $rSO_2$ is more than 70% while the standard calculation produces estimation $rSO_2$=10%. This indicates that background absorption with the nonlinear characteristics is present.

For the data on FIG. 5 $OD''_{Deep-Shall}$ (730 nm)/$OD''_{Deep-Shall}$ (770 nm)=−3.3 indicating the $rSO_2$ is less than 60%. While the standard calculation produces an estimation of $rSO_2$=56%. This indicates that there is no background absorption with the nonlinear characteristics.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the disclosure is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system for assessing tissue blood oxygen saturation levels, comprising:
   a computing device;
   a sensor in communication with said computing device, said sensor being configured to be attached to a human subject and having:
      a light source capable of selectively emitting at least four different wavelengths of light, one wavelength at a time; and
      a first light detector positioned a first distance from said light source and a second light detector positioned a second distance from said light source, said second distance being greater than said first distance;
   said computing device having a memory for storing an algorithm and a processor for executing instructions associated with said algorithm, said algorithm comprising the following steps:
   causing said light source to emit light of at least four different wavelengths, one wavelength at a time, into a human subject;
   receiving optical density measurements from said first and second light detectors for each of the four wavelengths;
   calculating a space contrasted ratio of the wavelength contrast difference of the optical density based on the optical density measurements from said first and second light detectors for three of said wavelengths emitted by said light source;
   estimating a first tissue blood oxygen saturation value based on said space contrasted ratio of the wavelength contrast difference of the optical density;
   calculating a second order contrasted optical density ratio based on the optical density measurements from said first and second light detectors for at least four of said wavelengths emitted by said light source;
   estimating a second tissue blood oxygen saturation value based on said second order contrasted optical density ratio; and
   determining if said first tissue blood oxygen saturation value is a valid estimate of an actual tissue blood oxygen saturation level in said human subject based upon a comparison of said first blood oxygen saturation value and said second blood oxygen saturation value.

2. The system of claim 1, wherein said first tissue blood oxygen saturation value is determined to be a valid estimate of said actual tissue blood oxygen saturation level if said first tissue blood oxygen saturation value is about the same as said second tissue blood oxygen saturation value.

3. The system of claim 1, wherein said first tissue blood oxygen saturation value is determined to be an invalid estimate of said actual tissue blood oxygen saturation level if said first tissue blood oxygen saturation value is at least about 10% or more different than said second tissue blood oxygen saturation value.

4. The system of claim 1 wherein said space contrasted ratio of the wavelength contrast difference of the optical density is calculated by applying the following equation:

$$OD'_{Deep\text{-}Shall}(\lambda 1)/OD'_{Deep\text{-}Shall}(\lambda 2)$$

where $OD'(\lambda) = OD(\lambda) - OD(\lambda+\Delta)$ is the wavelength contrasted optical density that can be described as a wavelength contrast difference of the optical density $OD(\lambda)$; and $OD_{Deep\text{-}Shall}(\lambda) = OD_{Deep}(\lambda) - OD_{Shallow}(\lambda)$ is the spatial contrasted optical density that is the difference of the optical density measured by the far detector $OD_{Deep}(\lambda)$ and the near detector $OD_{Shallow}(\lambda)$ at wavelength $\lambda$.

5. The system of claim 1 wherein said second order contrasted optical density ratio is calculated by applying the following equation:

$$OD''_{Deep\text{-}Shall}(\lambda)/OD''_{Deep\text{-}Shall}(\lambda+\Delta)$$

where $OD''_{Deep\text{-}Shall}(\lambda) = OD_{Deep\text{-}Shall}(\lambda+\Delta) - 2*OD_{Deep\text{-}Shall}(\lambda) + OD_{Deep\text{-}Shall}(\lambda-\Delta)$.

6. The system of claim 1 wherein said second order contrasted optical density ratio is calculated by applying the following equation:

$$OD''_{Deep\text{-}Shall}(\lambda)/OD_{Deep\text{-}Shall}(\lambda+\Delta)$$

where $OD''_{Deep\text{-}Shall}(\lambda) = OD_{Deep\text{-}Shall}(\lambda+\Delta) - 2*OD_{Deep\text{-}Shall}(\lambda) + OD_{Deep\text{-}Shall}(\lambda-\Delta)$, and
where $OD_{Deep\text{-}Shall}(\lambda) = OD_{Deep}(\lambda) - OD_{Shallow}(\lambda)$.

7. The system of claim 1 wherein said second order contrasted optical density ratio is calculated by applying the following equation:

$$OD''_{Deep\text{-}Shall}(\lambda)/[OD_{Deep\text{-}Shall}(\lambda+\Delta)+B]$$

where $OD''_{Deep\text{-}Shall}(\lambda) = OD_{Deep\text{-}Shall}(\lambda+\Delta) - 2*OD_{Deep\text{-}Shall}(\lambda) + OD_{Deep\text{-}Shall}(\lambda-\Delta)$,
where $OD_{Deep\text{-}Shall}(\lambda) = OD_{Deep}(\lambda) - OD_{Shallow}(\lambda)$, and
where B is an empirical constant.

8. The system of claim 1 wherein said algorithm further comprises the step of calculating a valid tissue blood oxygen saturation level if it is determined that said first tissue blood oxygen saturation value is invalid.

9. The system of claim 8, wherein said calculation of a valid tissue blood oxygen saturation level is based on a measurement of optical density of reflected light having a wavelength greater than 837 nm.

10. The system of claim 8, wherein said computing device further includes a visual display device and said algorithm further includes the step of causing said valid tissue blood oxygen saturation level to be displayed on said display device.

* * * * *